US010288575B2

(12) United States Patent
Ali et al.

(10) Patent No.: US 10,288,575 B2
(45) Date of Patent: May 14, 2019

(54) ENVIRONMENT SENSOR SYSTEM

(71) Applicant: AMS Sensors UK Limited, Cambridge, Cambridgeshire (GB)

(72) Inventors: Syed Zeeshan Ali, Cambridge (GB); Simon Jonathan Stacey, Ely (GB); Florin Udrea, Cambridge (GB)

(73) Assignee: AMS SENSORS UK LIMITED, Cambridge, Cambridgeshire (GB)

( * ) Notice: Subject to any disclaimer, the term of this patent is extended or adjusted under 35 U.S.C. 154(b) by 234 days.

(21) Appl. No.: 15/168,547

(22) Filed: May 31, 2016

(65) Prior Publication Data

US 2017/0343502 A1   Nov. 30, 2017

(51) Int. Cl.
*G01N 27/18* (2006.01)
*H05B 1/02* (2006.01)
*G01N 21/3504* (2014.01)
*G01N 27/12* (2006.01)
*G01N 27/16* (2006.01)
*G01N 21/03* (2006.01)

(52) U.S. Cl.
CPC ......... *G01N 27/18* (2013.01); *G01N 21/0332* (2013.01); *G01N 21/3504* (2013.01); *G01N 27/123* (2013.01); *G01N 27/16* (2013.01); *H05B 1/0288* (2013.01); *G01N 2201/06186* (2013.01)

(58) Field of Classification Search
None
See application file for complete search history.

(56) References Cited

U.S. PATENT DOCUMENTS

| 5,255,556 A | 10/1993 | Lobdell |
| 5,834,777 A * | 11/1998 | Wong ................. G01N 21/0303 250/343 |
| 6,276,192 B1 | 8/2001 | Sim |
| 8,931,950 B2 * | 1/2015 | King .................... G01K 17/006 374/121 |

(Continued)

FOREIGN PATENT DOCUMENTS

| EP | 2767881 A1 | 8/2014 |
| GB | 2046921 A | 11/1980 |
| GB | 2464016 A | 4/2010 |

OTHER PUBLICATIONS

International Search Report and Written Opinion dated Aug. 18, 2017 for corresponding International Application No. PCT/GB2017/051469.

(Continued)

*Primary Examiner* — Paul M. West
*Assistant Examiner* — Mark A Shabman
(74) *Attorney, Agent, or Firm* — Tarolli, Sundheim, Covell & Tummino LLP

(57) ABSTRACT

We disclose herein an environmental sensor system comprising an environmental sensor comprising a first heater and a second heater in which the first heater is configured to consume a lower power compared to the second heater. The system also comprises a controller coupled with the environmental sensor. The controller is configured to detect if a measured value of a targeted environmental parameter is present. The controller is configured to switch on at least one of the first and second heaters based on the presence and/or result of the measured value of the targeted environmental parameter.

26 Claims, 11 Drawing Sheets

(56) References Cited

U.S. PATENT DOCUMENTS

2010/0152993 A1* 6/2010 Antel, Jr. ............ F02D 41/0045
                                                    701/103
2014/0212979 A1   7/2014 Burgi
2015/0285772 A1* 10/2015 Park ................... G01N 33/0031
                                                    73/31.05

OTHER PUBLICATIONS

Gardner J W: "A Gas Sensor System for Harsh Environment Applications", Procedia Engineering, vol. 120, Sep. 9, 2015, pp. 275-278.
Fort A: "Selectivity Enhancement of SnO"2 Sensors by Means of Operating Temperature Modulation", Thin Solid F, Elsevier, Amsterdam NL, vol. 418, No. 1, Oct. 1, 2002, pp. 2-8.

* cited by examiner

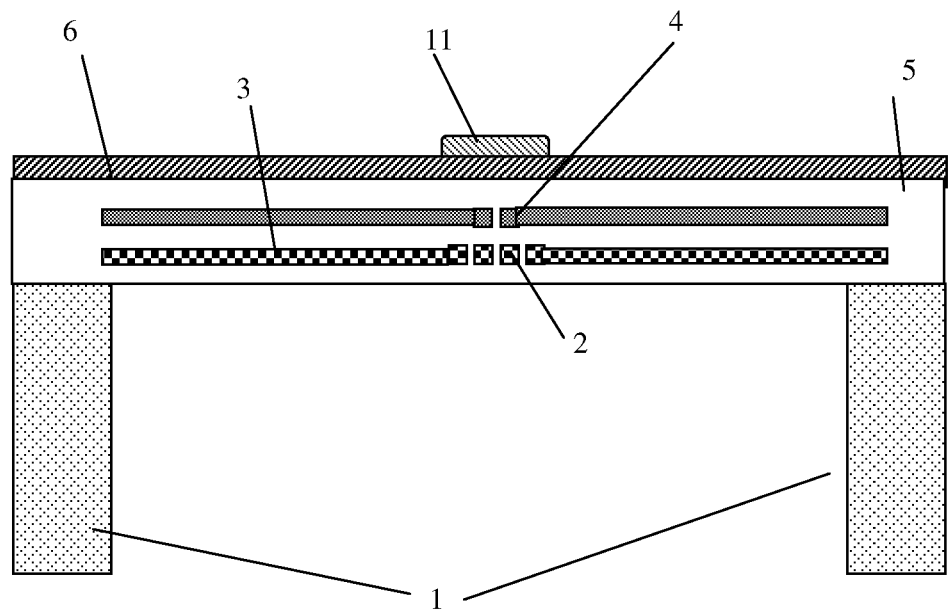
Figure 15
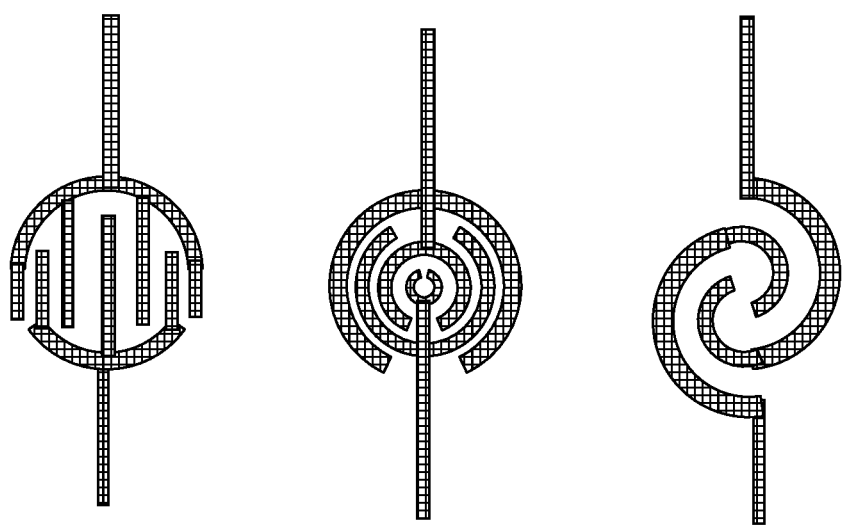
Figure 16 (a) (b) (c)

ENVIRONMENT SENSOR SYSTEM

FIELD OF THE INVENTION

The invention generally relates to an environmental sensor system, particularly but not exclusively, the invention relates to gas sensing devices and a method for operating gas sensing devices.

BACKGROUND OF THE INVENTION

It is known to fabricate gas sensors based on resistive gas sensing, calorimetric gas sensing or Non Dispersive Infra-Red (NDIR) based gas sensing. Each of these sensors requires a heater.

In the resistive gas sensor, the heater heats the sensing material to a high temperature, at which the resistance of the material changes in presence of gas. In a calorimetric sensor, the heater heats a catalyst, and the temperature of the device increases in the presence of the target gas. In an NDIR sensor, a heater is used to provide Infrared radiation which is detected by an IR detector. The IR detector detects how much radiation has been absorbed by the target gas in the path between the emitter and detector to determine the gas concentration.

The heater used can either be a bulk device, such as a filament wire or in the case of NDIR sensors a micro-bulb. Alternately it can be fabricated on a semiconductor chip, for example as a micro-hotplate, where a heater is embedded within a dielectric membrane supported by a semiconductor substrate.

The biggest source of power consumption in these sensors is the use of the heater. As such different methods have been used to reduce the power consumption. One method used is to have a low power and a high power mode of operating the sensor. When the measured results indicate a low concentration of gas, the sensor operates in a low power mode, whereas when the results indicate a presence or high concentration of gas, then the sensor is operated in a high power mode (U.S. Pat. No. 5,255,556, EP2762881). An example different modes is to vary the frequency of measurement, for example having a high frequency of measurement during the high power mode, and having a low frequency of measurement during the low power mode. Changes in the pulse width of the measurement are also possible to achieve this.

SUMMARY

In this invention, we disclose a further method for improved control of operating the gas sensor to achieve good sensitivity while having low power consumption. In each of the sensor types, the size and operation of the heater used is important. If a large heater is used, then the power consumption of the sensor is relatively high. However, if the heater is small, then the sensitivity of the sensor is typically low.

We disclose a method of operating a gas sensor where: the gas sensor comprises at least two heaters of different sizes; and depending on the obtained gas sensing measurement, decide which heater or combination of heaters to turn on.

According to one aspect of the present invention, there is provided an environmental sensor system comprising:
  an environmental sensor comprising at least a first heater and a second heater, wherein the first heater is configured to consume a lower power compared to the second heater;
  a controller coupled with the environmental sensor, wherein the controller is configured to switch on at least one of the first and second heaters based on a predetermined technique.

The controller may be configured to apply the predetermined technique to detect if a measured value of a targeted environmental parameter is present, and wherein the controller is configured to switch on at least one of the first and second heaters based on the presence and/or result of the measured value of the targeted environmental parameter.

The controller may be configured to apply the predetermined technique to switch on at least one of the first and second heaters based on a time based event or based on a power change detection in the sensor system.

The first heater may have a smaller size compared to the second heater. The controller may be configured to detect if there is no measured value of the targeted environmental parameter. The controller may be configured to switch on the first heater. It will be appreciated that the invention is not restricted to only two heaters—any number of heaters more than two heaters are possible. The skilled person would understand that when more than two heaters will be incorporated each of the heaters will have different power consumption level.

The controller may be configured to analyse the measured value and if the measured value exceeds a predetermined threshold limit the controller is configured to switch on the second heater.

The controller may be configured to switch on both the first and second heaters if the measured value exceeds the predetermined threshold limit.

The controller may be configured to:
  store a set of measured values;
    analyse a predetermined number of recent measured values from the set of measured values; and
    determine which of the first and second heaters to be switched on based on the analysed results of the predetermined number of recent measured values.

The controller may be configured to switch on the first heater if the controller determines from the analysed results that there are no measured values or the measured values are less than a pre-determined threshold limit.

The controller may be configured to switch on the second heater or both the first and second heaters if the controller determines from the analysed results that the measured values are more than a pre-determined threshold limit.

The environmental sensor may comprise:
  a substrate comprising an etched portion;
  a dielectric region on the substrate, the dielectric region being formed such that a dielectric membrane is formed adjacent the etched portion;
  wherein the first and second heaters are formed in or on the dielectric membrane.

The environmental sensor may comprise:
  a substrate comprising a first etched portion and a second etched portion;
  a dielectric region on the substrate, the dielectric region being formed such that a first dielectric membrane is formed adjacent the first etched portion and a second dielectric membrane is formed adjacent the second etched portion;
  wherein the first heater is formed in or on the first dielectric membrane, and the second heater is formed in or on the second dielectric membrane.

The environmental sensor may be a humidity sensor.

The first and second heaters may be formed in one or more of the following configurations
  concentrically to one another;

on top of one another; and laterally spaced to one another.

According to a further aspect of the present invention, there is provided a method for controlling an environmental sensor, the sensor comprising at least a first heater and a second heater, wherein the first heater consumes a lower power compared to the second heater; the method comprising: switching on at least one of the first and second heaters based on a predetermined technique.

The method may further comprise: detecting if a measured value of a targeted environmental parameter is present, and switching on at least one of the first and second heaters based on the presence and/or result of the measured value of the targeted environmental parameter.

In one embodiment of the invention, the environmental sensors is a gas sensor and comprises two heaters—a large heater (second heater) and a small heater (first heater). The gas sensor could be a resistive gas sensor, a calorimetric gas sensor or an NDIR sensor. Typically in such sensor a large heater consumes more power, but also has better sensitivity as it heats a larger sensing area. Such a sensor may operate by normally having only the small heater turned on to conserve power, but switching to the large heater (or turning on both heaters) when it detects the presence of the target gas. Additionally, the smaller heater is likely to have a lifetime and improve reliability compared to the larger heater and since this heater is operated for a longer time, the overall system is expected to have improved reliability without compromising on the sensitivity.

There can be various implementations of such a method. For example, a simple method could be that if the last measure value suggested a presence, or a relatively high concentration of the target gas, then the large heater should be operating, but if the last measured value suggests absence, or a relatively low concentration of the target gas then only the small heater should be in operation. A more complex method could look at the last few measured readings (for example 5 or 10 readings) to make a decision of which heater should be turned on. Even more complex methods could look at even longer periods of time to make a decision. Such complex methods could also take into account the humidity and ambient temperature levels as well as the level of gas detected, Alternatively, switching between heaters could be predetermined rather than based on results in order to provide potential discrimination of gases and environmental interferers such as temperature and humidity. In the case of more than two heaters of different sizes, various methods can be used to determine which heater or heaters need to be on depending on the results of previous measurements.

An example of such a sensor is a resistive gas sensor. The sensor may consist of a large and a small heater both coated with a sensing material, whose resistance and/or capacitance changes in the presence of the target gas. There are also electrodes to measure the resistance and/or capacitance of the sensing material. The larger heater can heat a larger amount and a larger surface area of sensing material, hence increasing its sensitivity and accuracy. The sensing material can be a metal oxide, for example, tin oxide, tungsten oxide, zinc oxide and molybdenum oxide. The sensing material can also be either a polymer, or a nano-material such as carbon nanotubes, graphene, or metal oxide nanowires. Furthermore, the sensing material may also be doped or mixed with different materials or metals, such as palladium or platinum. The sensing material heated by the heaters can either be the same on all the heaters, or can be different. Such a sensor can also be a resistive humidity sensor.

Alternately, the sensor could be a calorimetric gas sensor. In this case the heaters are coated with a catalyst which causes a small increase in heater temperature in the presence of the target gas. The larger heater can heat a larger amount of catalyst, hence increasing its sensitivity. The catalyst can be a metal such as palladium or platinum. The catalyst heated by the heaters can either be the same on all the heaters, or can be different.

As another option, the sensor could be a non-dispersive infrared (NDIR) sensor, where the heaters are used as an Infrared (IR) source. The sensor comprises an optical path with an IR source and an IR detector at either end. The absorption of particular wavelengths of IR by the target gas can be detected by the detector (a filter is used to limit the wavelengths reaching the detector) to determine gas presence or concentration. A larger heater means a higher amount of IR radiation is emitted, resulting in a higher signal to noise ratio, and hence higher sensitivity. The IR detector used can be a diode, bolometer, pyrodetector, or a thermopile.

The heaters could be fabricated on a semiconductor substrate as a micro-hotplate structure. This comprises a heater embedded within a dielectric membrane supported by a semiconductor substrate. The different sized heater can either be on the same membrane, or on separate membranes, or a combination. Furthermore, the different sized heaters may be defined on the same layer within the membrane or membranes or on different layers within the membrane or membranes. In case the different sized heaters are on separate membranes, the membranes can also be of different sizes. For example the smaller heater can be implemented on a smaller membrane while the larger heater on a larger membrane.

There can also be a temperature sensor embedded within the membrane to measure the heater temperature. This sensor can be a diode, or a resistive sensor made of single crystal silicon, polysilicon, or a CMOS compatible metal such as aluminium, tungsten, titanium, copper, or can be a non-CMOS metal such as gold or platinum.

In the case of resistive gas sensors, there can be electrodes above or below the membrane there the sensing material is deposited. In the case of the different sized heaters on the same membrane, there can be either a single set of electrodes, or a set of large and small electrodes, which are activated depending on whether the large or small heater is operating. The electrodes can be interdigitated, or maybe a few electrodes side by side. The electrodes can be arranged in a circular or rectangular configuration.

In case of calorimetric gas sensors, the catalytic material can be deposited within the heater area either above or below the membrane. Electrodes are not needed in this case.

The heater can be a metal resistive heater, or can be a MOSFET heater, or can be a single crystal silicon heater or a polysilicon heater. The heater maybe made of a CMOS metal such as tungsten, aluminium, titanium or copper or a combination of these metals. Alternately it can be made from a non-CMOS metal such as platinum or gold. Similarly in the case of a resistive heater, the electrodes maybe made from any metal, for example, tungsten, aluminium, titanium, copper, platinum or gold. There may also be additional layers in the heater or electrode metal to improve adhesion to the dielectric membrane. The heater can be circular or rectangular, and maybe of any shape such as meander, spiral, ring or multi-ring. The heaters maybe formed of the same material and layer, or maybe formed of different materials and/or layers.

The membrane can be made of one or more dielectric materials, for example silicon dioxide, silicon nitride and/or aluminium oxide or a combination of these materials. The membrane may also have a temperature sensor embedded within the membrane. This can either be a diode, a resistive heater or a thermopile. The membrane may also have a heat spreading plate embedded within it—which is a metal plate within the heater area to improve the temperature uniformity of the heater. The membrane can be of any shape such as circular, square, rectangular, or rectangular with rounded corners.

The membrane can be formed by a bulk front or back side etch of the supporting substrate. The membrane can be a suspended membrane, supported by two or more beams. The membrane can also be a "closed membrane", supported along its entire perimeter by the substrate. The membrane trench can have sloping sidewalls—formed using anisotropic wet etching methods such as potassium hydroxide (KOH) or Tetramethylammonium hydroxide (TMAH) The membrane can also have vertical or near vertical sidewalls, formed by dry etching, such as deep reactive ion etching (DRIE).

There may also be an array of such sensors. The sensor can either be all on one chip, or can be separate. Each sensor in the array may have a different sensing material, and may have a set of different sized heaters. In such an array, the decision to select the heater for each sensor maybe made based on the measured results of that sensor. Alternately, the decision maybe made collectively for the entire array based on the previous measurements for the whole array. This may give the same operating conditions for the entire array (for example, all sensors operate either the large heater, or all operate the small heater). Alternately, it may give different operating conditions for each sensors, for example some sensors may operate the large heater, or some a small heater. Many such configuration modes can be setup for the array.

The heaters can be operated either in DC or in pulsed mode, such as PWM (Pulse Width Modulation) mode or frequency modulation mode. The heater operation can also consist of a series of pulses at different temperatures. Aside from switching between heaters, intelligent algorithms may also be used to vary the pulse frequency, duty cycle or amplitude of the voltage or the current applied to the heaters, or the temperature of the heater to vary the power consumption, or the sensitivity of the sensor.

Alternatively, the two or more heaters can also be used to create different thermal constant times due to different thermal masses). When operated in an AC, dynamic mode it is possible to detect selectively different species of gases which have different chemical reaction times. In this way the two heaters can be used to improve the selectivity of the device.

For example, a resistive gas sensor can be used in an environment where there is a need to distinguish between one of two gases that maybe present. The gases can be such that they both react to the sensing material, but at different reaction rates. Most of the time, the small heater is operated normally in AC mode, or pulsed mode. During this operation, the gas may absorb and desorb as the heater turns on or off depending on the pulse. This will change the resistance of the sensing material, and the variation of this resistance with respect to time will be a pattern characteristic of the heater size as well as the gas.

When it detects the presence of a gas, the sensor switches to using the larger heater. The larger heater has a greater thermal mass and a slower thermal response time. So the variation of resistance with respect to time will be a different pattern compared to the smaller heater. These different patterns between the heaters will allow distinguishing between the two gases, as well as the ratio in the case that both gases are present.

The method can be extended to more than two gases, and to having more than two heaters. Furthermore, once the larger heater (the second heater) is operating, the sensor may switch occasionally to the smaller heater (the first heater) to get the characteristic response curves of both the heaters.

The gas sensor or array of gas sensors may be connected to interface circuitry on the same chip, or on a separate chip within the same package.

The decision of which heater or heaters need to be controlled can be taken by circuitry on the same chip, or same package, or same PCB. The decision may also be taken by a micro-controller, a micro-processor, or a processing unit in a remote location.

The gas sensor may be part of a portable electronic device such as a phone, a tablet, laptop or a watch. The gas sensor may also be used in air quality monitoring applications in building or other consumer devices.

BRIEF DESCRIPTION OF THE PREFERRED EMBODIMENTS

FIGS. 13-15 show the schematic cross-section of different designs of gas sensors with two heaters in the same membrane.

FIG. 16 shows different design of electrodes for resistive gas sensors.

DETAILED DESCRIPTION OF THE PREFERRED EMBODIMENTS

Figure 1:
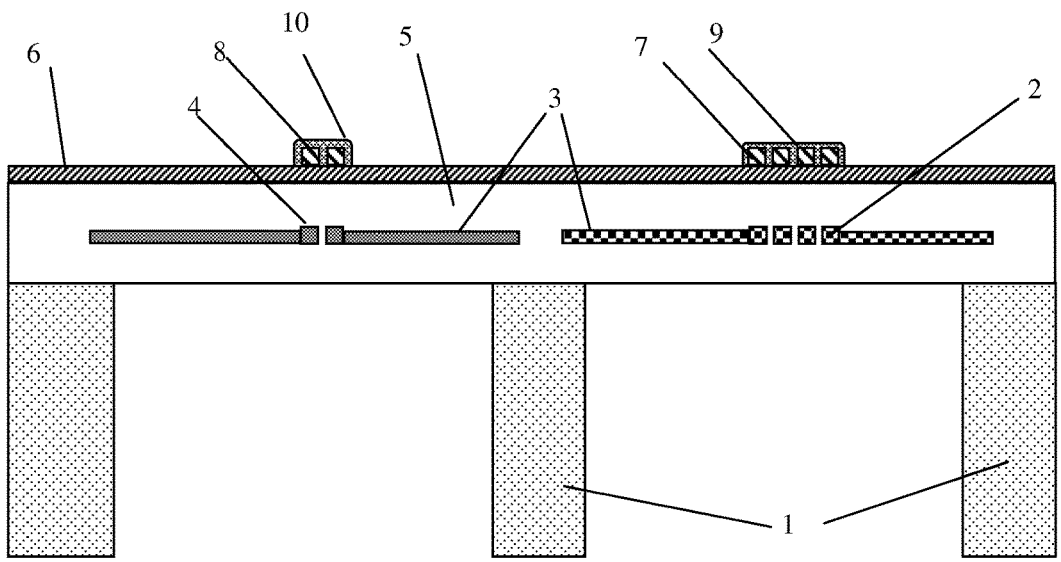
FIG. 1 shows the schematic cross-section of a resistive gas sensor with two micro-hotplates, one having a large heater, and one having a small heater.

FIG. 1 shows the schematic cross-section of a resistive gas sensor comprising two micro-hotplates, supported on a silicon substrate 1. One micro-hotplates has a large heater 2 (the second heater) embedded within the membrane, and electrodes 7 on top of the membrane. A sensing material 9 is deposited on top of the electrodes 7. The other micro-hotplate has a small heater 4 (the first heater) embedded within the membrane, and electrodes 8 on top of the membrane. A sensing material 10 is deposited on top of the electrodes 8.

When gas is not present, then the small heater 4 will be powered, and the resistance of the sensing material 10 will be measured. If the measured resistance of the material 10 indicates a presence of gas, then heater 2 will be powered instead and the resistance of sensing material 9 measured.

Figure 2:
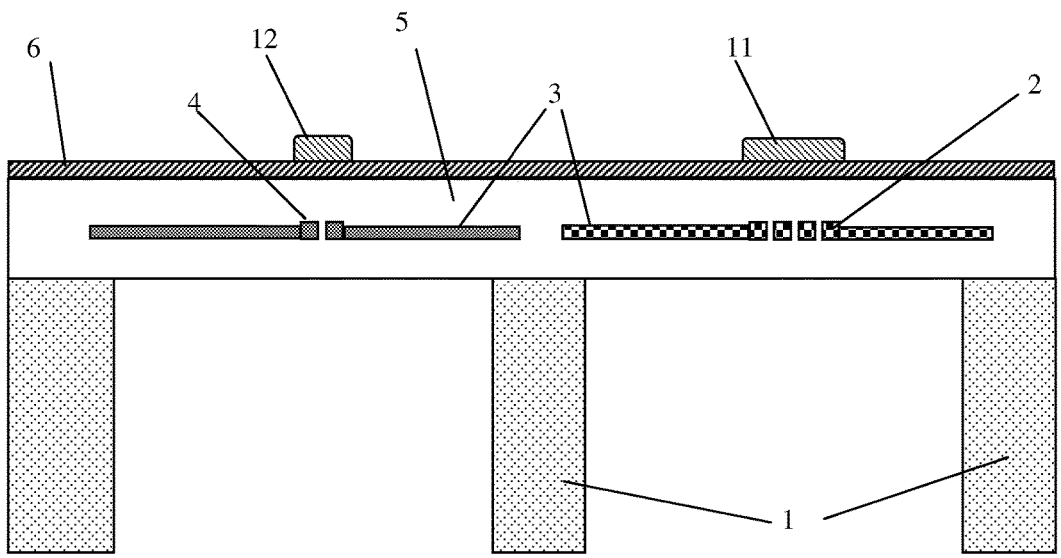
FIG. 2 shows the schematic cross-section of a calorimetric gas sensor with two micro-hotplates, one having a large heater, and one having a small heater.

FIG. 2 shows the schematic cross-section of a calorimetric gas sensor comprising two micro-hotplates. One hotplate has a large heater 2 embedded within the membrane, and a catalyst 11 on top of the membrane. The other hotplate has a small heater 4 embedded within the membrane and a catalyst 12 on top of the membrane.

Figure 3:
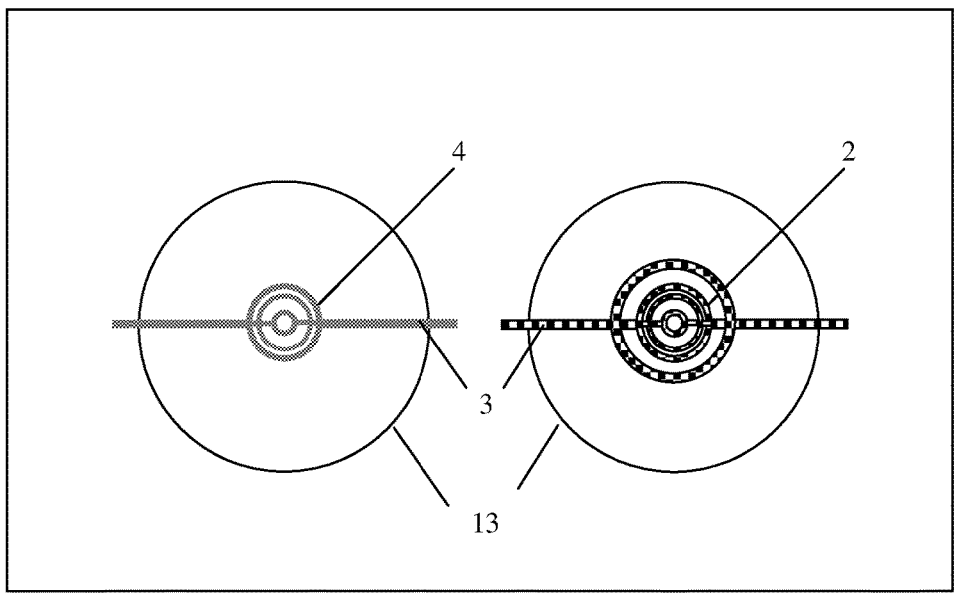
FIG. 3 shows the top-view of a calorimetric gas sensor with two micro-hotplates, one having a large heater, and one having a small heater.

FIG. 3 shows the top view of a calorimetric gas sensor comprising two micro-hotplates. Each hotplate comprises a heater and a membrane 13. The heaters and membranes are shown as circular, however they can also be square, or rectangular, or rectangular with rounded corners. The heaters can be of any shape such as meander, spiral, ring or multi-ring.

Figure 4:
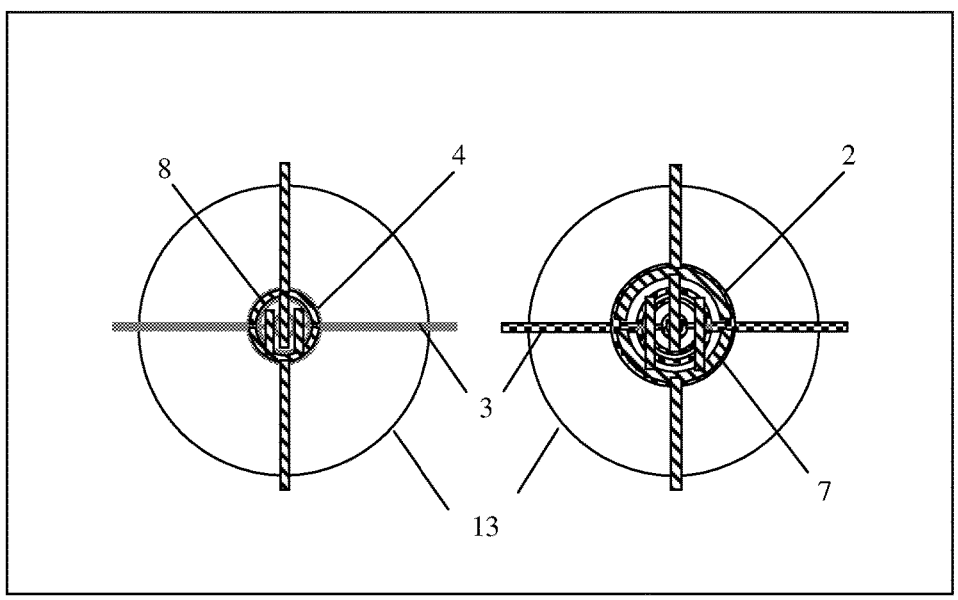
FIG. 4 shows the top-view of a resistive gas sensor with two micro-hotplates, one having a large heater, and one having a small heater.

FIG. 4 shows the top view of a resistive gas sensor comprising two micro-hotplates. Each hotplate comprises a membrane, and a heater embedded within the membrane, and electrodes on top of the membrane. The electrodes are shown as interdigitated, but they can be of many different shapes, including just to electrodes side by side.

Figure 5:
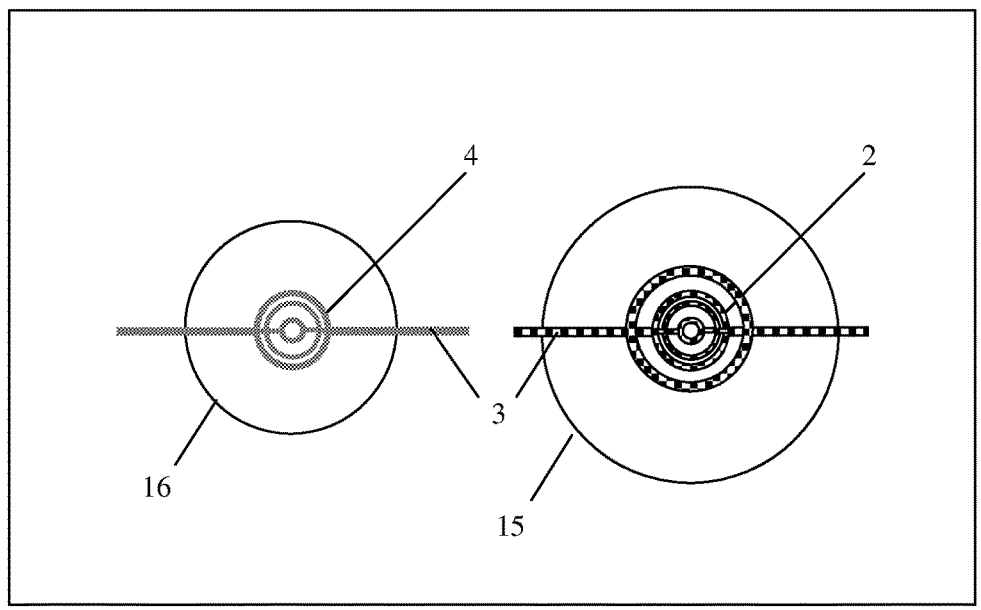
FIG. 5 shows the top-view of a calorimetric gas sensor with two hotplates having different heater and membrane sizes.

FIG. 5 shows the top view of a calorimetric gas sensor comprising two micro-hotplates. Each hotplate comprises a heater and a membrane. In this case the size of the membranes is different too as well as the heaters. One of the hotplates comprises a small heater 4 embedded within a small membrane 16, while the other hotplate comprises a larger heater 2 embedded within a large membrane 15.

Figure 6:
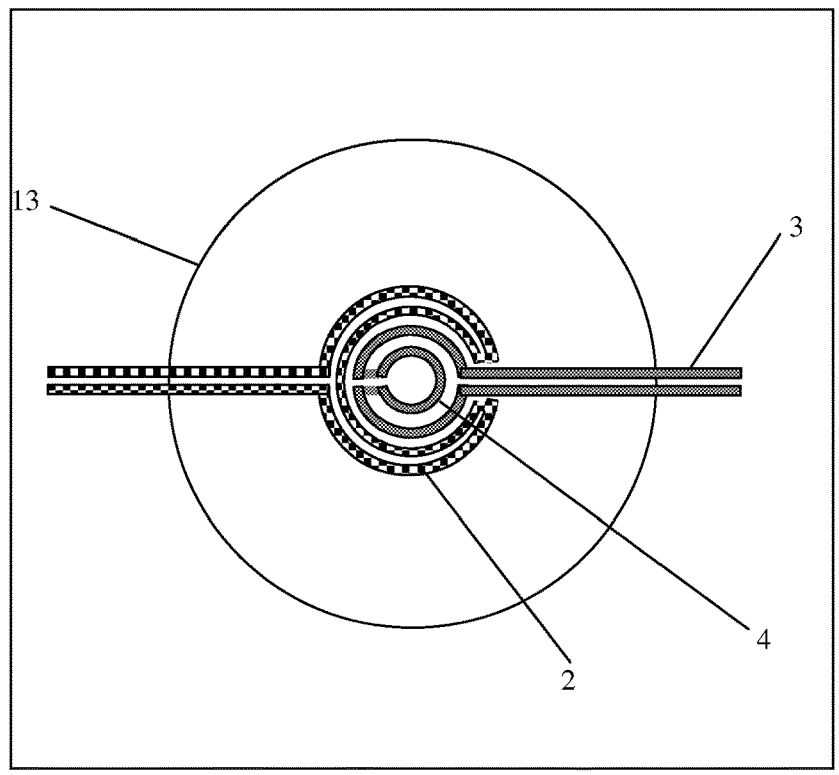
FIG. 6-8 show the top-view of a hotplate for calorimetric gas sensing, where there is a large and small heater on the same membrane.

FIG. 6 shows the top-view of a micro-hotplate for a calorimetric gas sensor with two heaters on the same membrane 13. One heater is large 2, and the other is small 4. The device can have a catalyst deposited on the membrane. When gas is not present, the small heater 4 (the first heater) maybe operated. When gas presence is detected, then either just the large heater 2 (the second heater) may be operated, or both the large 2 and small 4 heaters maybe operated.

Figure 7:
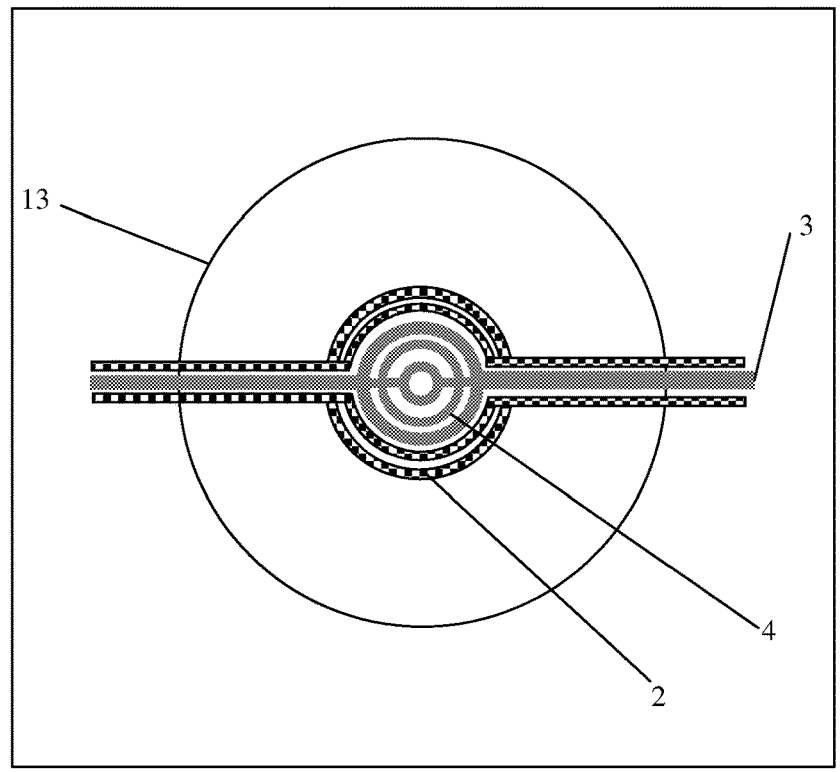

FIG. 7 shows the top view of a micro-hotplate for a calorimetric gas sensor with two heaters on the same membrane, having different sizes of the heaters. The large outer heater 2 comprises two parallel heaters.

Figure 8:
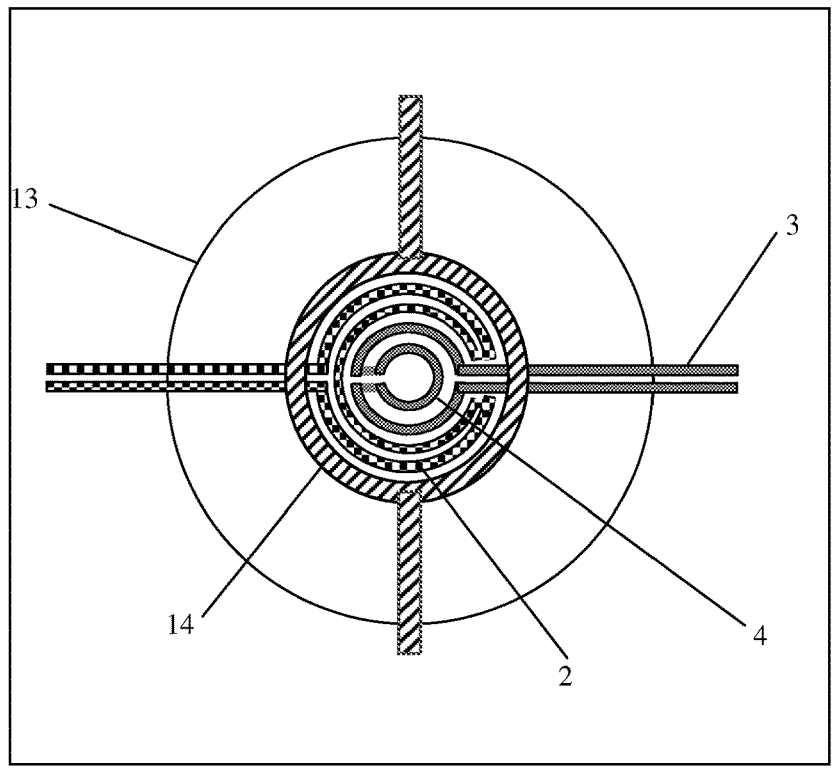

FIG. 8 shows the top view of a micro-hotplate for a calorimetric gas sensor with three heaters on the same membrane, having a different design of the heaters. The inner heater 4 is the smallest one, a larger ring heater 2 is outside, and a still larger heater 14 is also present (made on a different layer).

It should be noted that during operation when the larger heaters are operated, the smaller heaters may also be operated to improve the temperature uniformity within the heater region. Alternately the larger heaters can be on a different layer than the smaller heater allowing a more complicated design than just a ring to be made. Besides this many number and combination of heaters and heater designs are possible.

Figure 9:
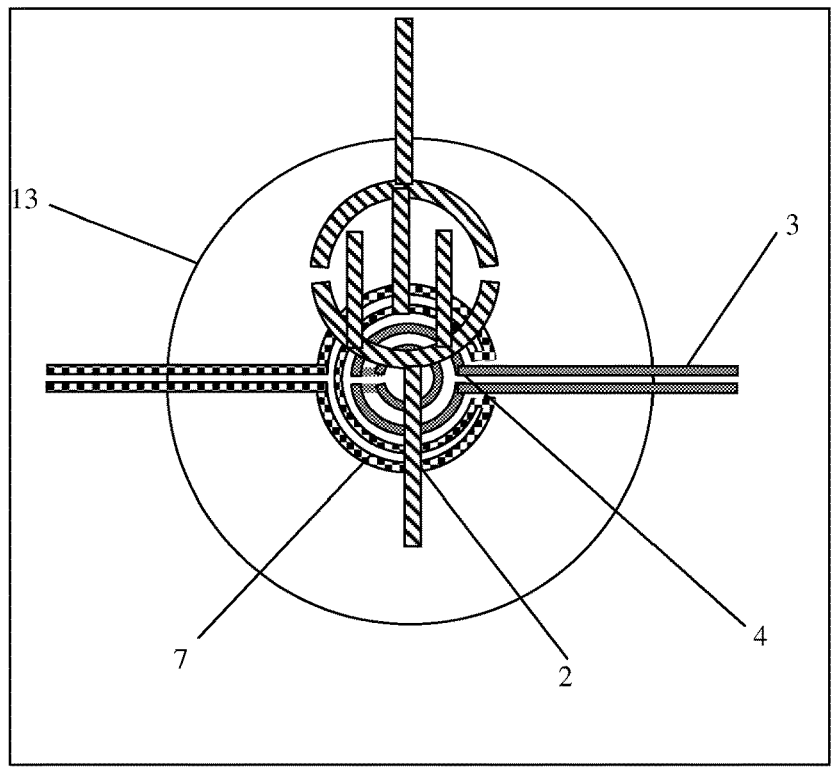
FIG. 9 shows the top-view of a hotplate for resistive gas sensing where there is a large and small heater on the same membrane

FIG. 9 shows the top view of a micro-hotplate for resistive gas sensors with two heaters on the same membrane. The design is the same as in FIG. 5, but has an addition of electrodes 7 on top of the membrane to measure the resistance and/or capacitance of the sensing material. There is only one set of electrodes 7 for both the large and small heater and can be used in all three heater operating configurations: (1) small heater 4 on, (2) large heater 2 on, (3) or both small 4 and large 2 heaters on.

Figure 10:
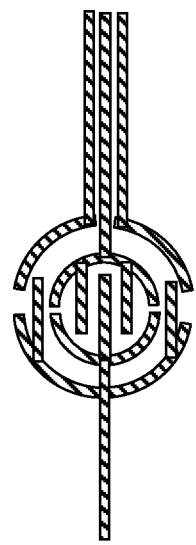
FIG. 10 shows the top-view of electrodes, meant for a hotplate with large and small heater on the same membrane.

FIG. 10 shows an example design of heater electrodes where the electrodes can be configured to either measure the resistance of the entire sensing material, or to just measure the resistance of the sensing material within the heater area.

Figure 11:
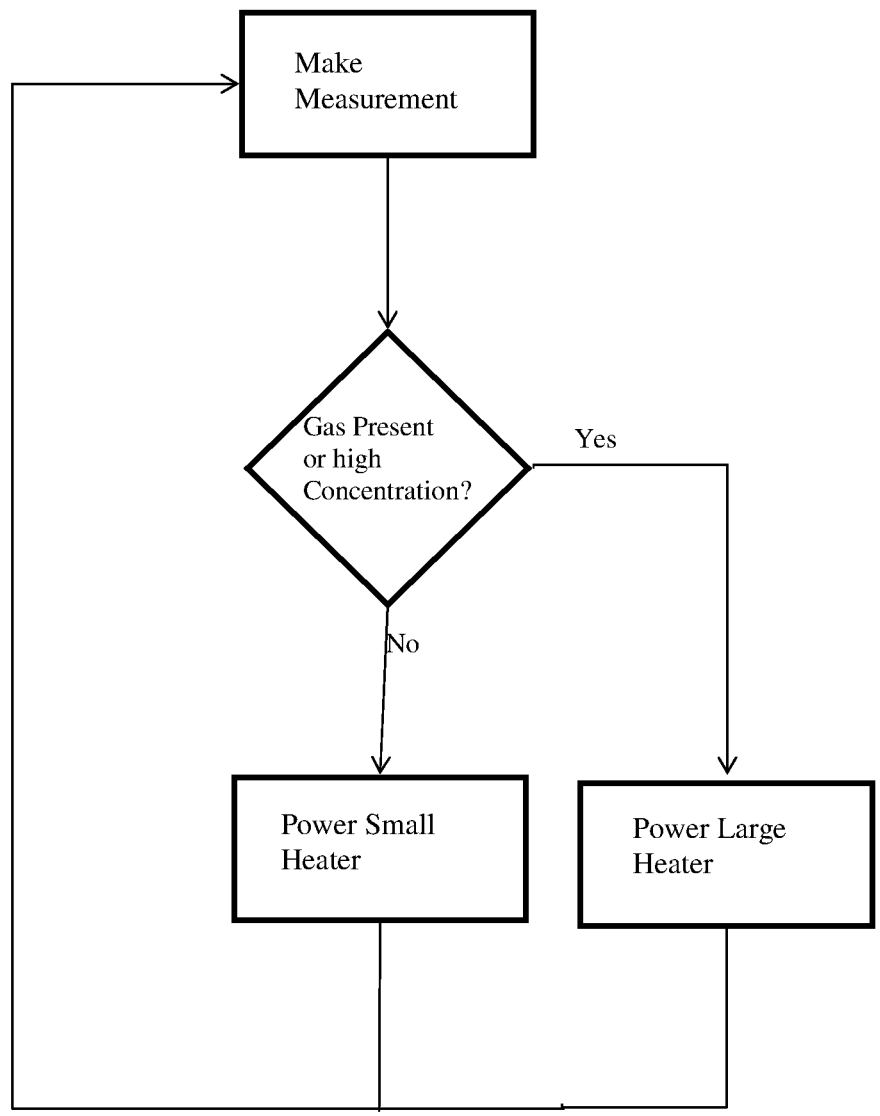
FIGS. 11 and 12 show example flow chart of operating the large and small heaters depending on results of gas sensing.

FIG. 11 shows the flow diagram of an example algorithm to control a gas sensor with a large and small heater. The gas sensor makes a measurement, and depending on the system, if gas is measured to be present, or above a certain concentration threshold, then the large heater is powered, then the next measurement made. Otherwise the small heater is powered (with the large one turned off), and the next measurement made.

Figure 12:
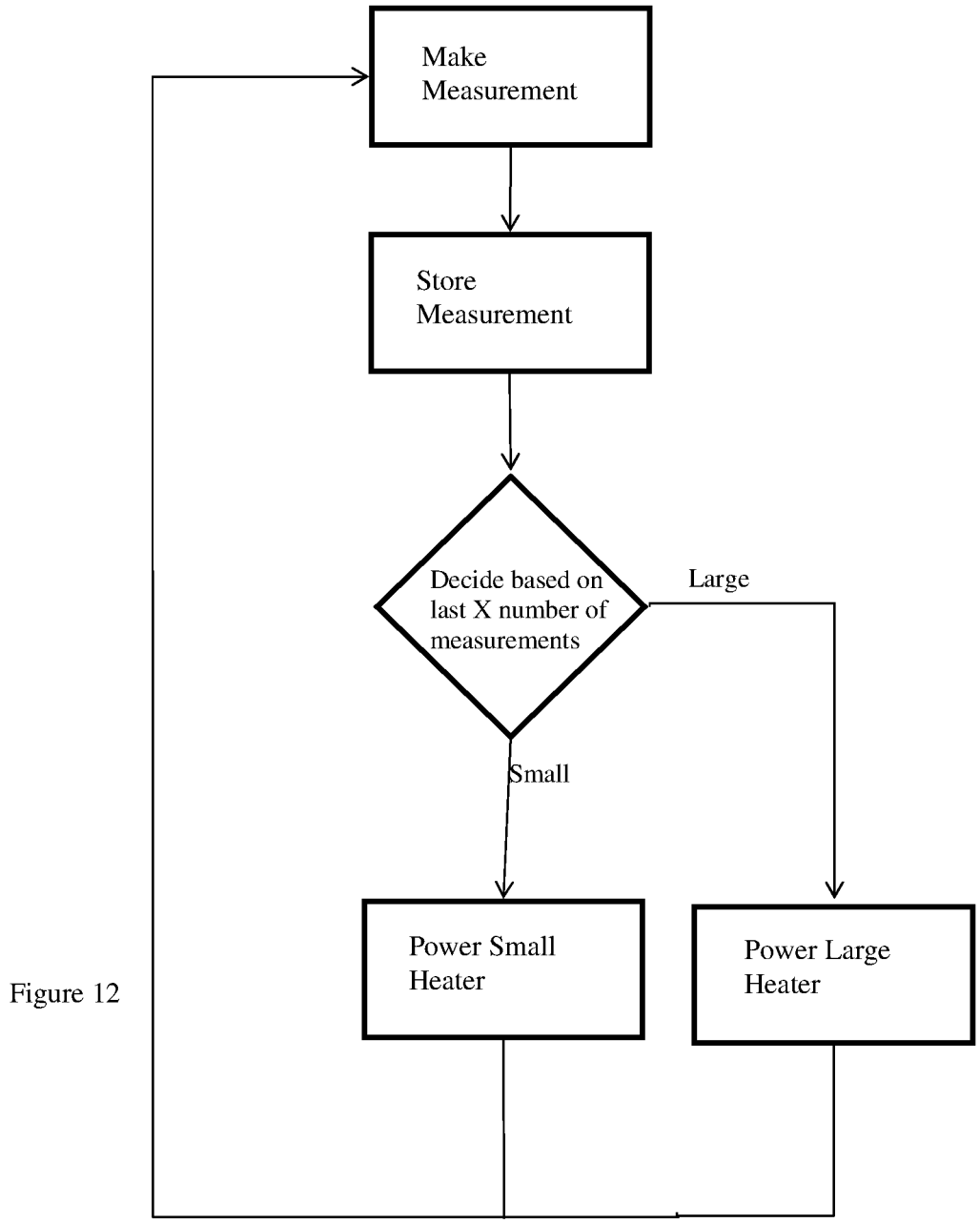

FIG. 12 shows the flow diagram of an example algorithm to control a gas sensor with a large and small heater. The gas sensor makes a measurement, and stores the value. Then it analyses the stored values from the last few measurements (the number can be defined in software) to determine whether the large or small heater should be on. Based on this decision either the large or small heater is powered, and the next measurement taken.

Figure 13:
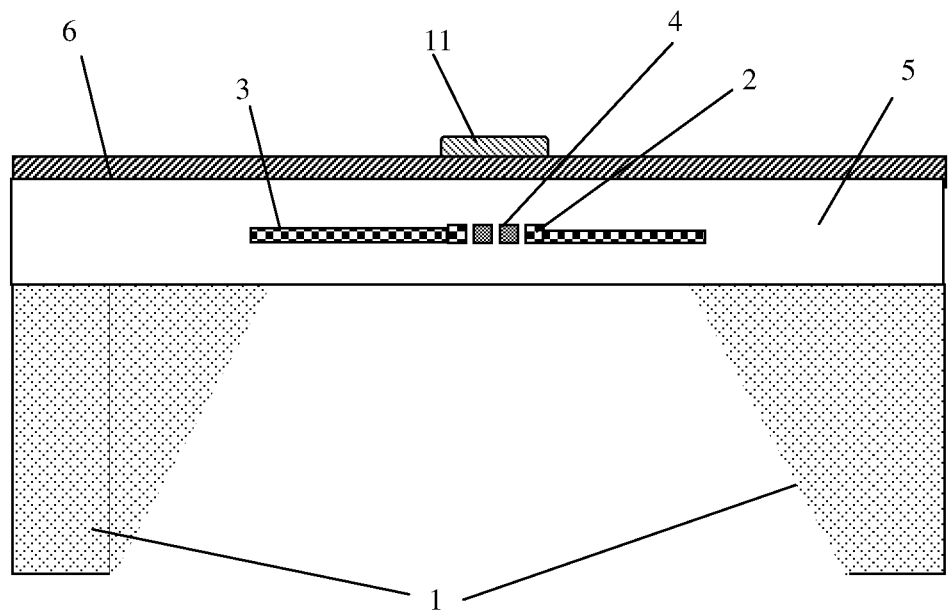

FIG. 13 shows the schematic cross-section of a gas sensor with a micro-hotplate where there is a large and small heater within the same membrane. In this case the membrane cavity has sloping sidewalls. This can be caused by wet anisotropic etching, for example using potassium hydroxide (KOH) or Tetramethylammonium hydroxide (TMAH).

Figure 14:
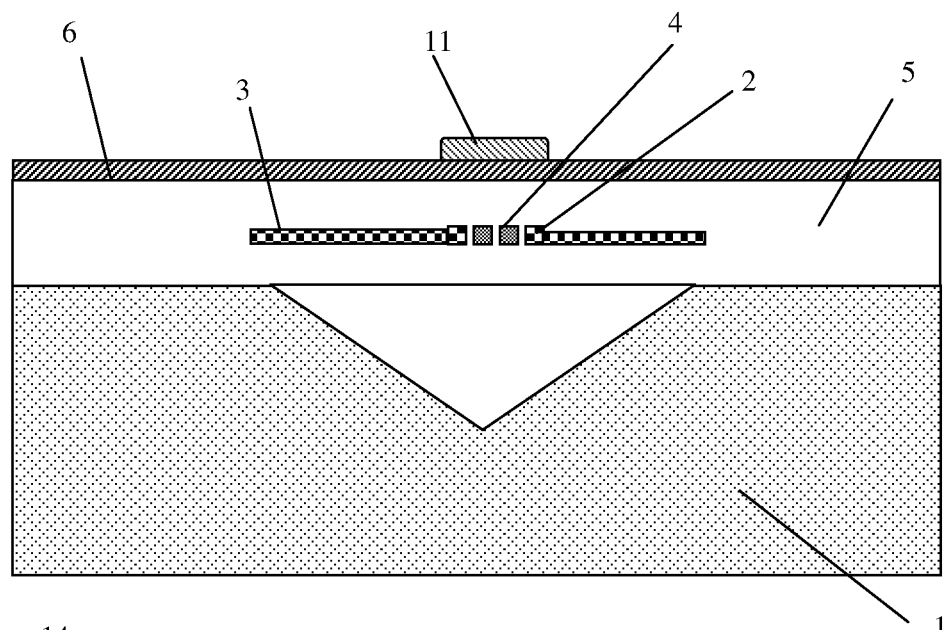

FIG. 14 shows the schematic cross-section of a gas sensor with a micro-hotplate where there is a large and small heater within the same membrane. In this case the membrane is a suspended membrane, and only supported by two or more beams, usually formed by a front side etch process.

FIG. 15 shows the schematic cross-section of a gas sensor with a micro-hotplate where there is a large and small heater within the same membrane, with each heater on a separate layer.

FIG. 16 shows different designs of electrodes on top of the membrane that are used to measure the resistance and/or capacitance of the sensing material in resistive gas sensors.

Figure 17:
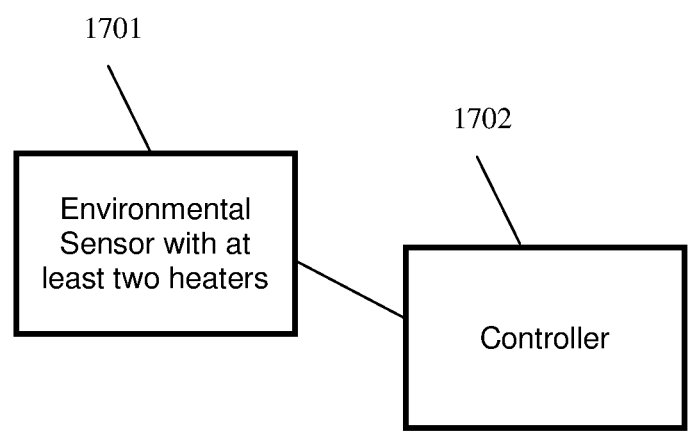
FIG. 17 is a schematic block diagram illustrating an environmental sensor and a controller coupled with the sensor.

FIG. 17 is a schematic block diagram illustrating an environmental sensor 1701 and a controller 1702 coupled with the sensor. The controller 1702 may be integrated with the sensor 1701, or the controller 1702 may be a discrete device coupled with the sensor 1701.

The skilled person will understand that in the preceding description and appended claims, positional terms such as 'above', 'below', 'front', 'back', 'vertical', 'underneath' etc. are made with reference to conceptual illustrations of a semiconductor device, such as those showing standard cross-sectional perspectives and those shown in the appended drawings. These terms are used for ease of reference but are not intended to be of limiting nature. These terms are therefore to be understood as referring to a semiconductor device when in an orientation as shown in the accompanying drawings.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. An environmental sensor system comprising:
an environmental sensor comprising at least a first heater and a second heater, wherein the first heater is configured to consume a lower power compared to the second heater;
a controller coupled with the environmental sensor,
wherein the controller is configured to switch on at least one of the first and second heaters based on a predetermined technique;
wherein the controller is configured to:
store a set of measured values;
analyse a predetermined number of recent measured values from the set of measured values; and
determine which of the first and second heaters to be switched on based on the analysed results of the predetermined number of recent measured values.

2. A sensor system according to claim 1, wherein the controller is configured to apply the predetermined technique to detect if a measured value of a targeted environmental parameter is present, and wherein the controller is configured to switch on at least one of the first and second heaters based on the presence and/or result of the measured value of the targeted environmental parameter.

3. A sensor system according to claim 1, wherein the controller is configured to apply the predetermined technique to switch on at least one of the first and second heaters based on a time based event or based on a power change detection in the sensor system.

4. A sensor system according to claim 1, wherein the first heater has a smaller size compared to the second heater.

5. A sensor system according to claim 1, wherein the controller is configured to detect if there is no measured value of the targeted environmental parameter.

6. A sensor system according to claim 5, wherein the controller is configured to switch on the first heater.

7. A sensor system according to claim 1, wherein the controller is configured to analyse the measured value and if the measured value exceeds a predetermined threshold limit the controller is configured to switch on the second heater.

8. A sensor system according to claim 7, wherein the controller is configured to switch on both the first and second heaters if the measured value exceeds the predetermined threshold limit.

9. A sensor system according to claim 1, wherein the controller is configured to switch on the first heater if the controller determines from the analysed results that there are no measured values or the measured values are less than a pre-determined threshold limit.

10. A sensor system according to claim 1, wherein the controller is configured to switch on the second heater or both the first and second heaters if the controller determines from the analysed results that the measured values are more than a pre-determined threshold limit.

11. A sensor system according to claim 1, wherein the environmental sensor comprises:
a substrate comprising an etched portion;
a dielectric region on the substrate, the dielectric region being formed such that a dielectric membrane is formed adjacent the etched portion;
wherein the first and second heaters are formed in or on the dielectric membrane.

12. A sensor system according to claim 11, wherein the dielectric membrane is formed by any one of:
back-etching using Deep Reactive Ion Etching (DRIE) of the substrate, and
using anisotropic etching such as Potassium Hydroxide (KOH) or TetraMethyl Ammonium Hydroxide (TMAH).

13. A sensor system according to claim 11, wherein the dielectric membrane comprises:
one or more dielectric layers comprising silicon dioxide and/or silicon nitride;
one or more layers of spin on glass, and
a passivation layer over the one or more dielectric layers.

14. A sensor system according to claim 11, wherein the sensor further comprises:
a sensing material in one side of the dielectric membrane; and
an electrode between the sensing material and the dielectric membrane.

15. A sensor system according to claim 14, wherein the sensor is a resistive gas sensor.

16. A sensor system according to claim 11, wherein the sensor is a calorimetric gas sensor, wherein a catalyst material is provided which is configured to increase a heater temperature when a targeted gas is present.

17. A sensor system according to claim 11, wherein the first and second heaters are formed in one or more of the following configurations:
concentrically to one another;
on top of one another; and
laterally spaced to one another.

18. A sensor system according to claim 1, wherein the environmental sensor comprises:
a substrate comprising a first etched portion and a second etched portion;
a dielectric region on the substrate, the dielectric region being formed such that a first dielectric membrane is formed adjacent the first etched portion and a second dielectric membrane is formed adjacent the second etched portion;
wherein the first heater is formed in or on the first dielectric membrane, and the second heater is formed in or on the second dielectric membrane.

19. A sensor system according to claim 1, wherein the sensor is a Non-Dispersive Infrared (NDIR) sensor, wherein the first and second heaters are configured to operate as Infrared (IR) sources.

20. A sensor system according to claim 1, wherein the environmental sensor is a humidity sensor.

21. A sensor system according to claim 1, wherein the first and second heaters are configured to operate in one or more of the following modes.

22. A sensor system according to claim 21, wherein the heaters are configured to operate using a series of pulses at a different temperature.

23. A sensor system according to claim 21, wherein the controller is configured to:
vary pulse frequency,
vary duty cycle or the amplitude of the voltage applied to the heaters; and
vary the temperature of the heaters.

24. A sensor system according to claim 1, wherein the first and second heaters are configured to operate in an alternative current (AC) mode or a dynamic mode.

25. A sensor system according to claim 24, wherein the controller is configured to detect different species of gases which have different chemical reaction rates.

26. A sensor system according to claim 25, wherein the controller is configured to operate the heaters such that two different gases are distinguished by analysing the chemical reaction rates.

* * * * *